(12) United States Patent
Fleissman et al.

(10) Patent No.: US 7,208,168 B2
(45) Date of Patent: Apr. 24, 2007

(54) SEGMENTED COMPOSITION AND A METHOD AND A SYSTEM FOR MAKING SAME

(75) Inventors: Leona G. Fleissman, Ridgewood, NJ (US); Anthony M. Santini, Yonkers, NY (US)

(73) Assignee: Avon Products, Inc, New York, NY (US)

( * ) Notice: Subject to any disclaimer, the term of this patent is extended or adjusted under 35 U.S.C. 154(b) by 107 days.

(21) Appl. No.: 11/124,502

(22) Filed: May 6, 2005

(65) Prior Publication Data

US 2005/0255136 A1 Nov. 17, 2005

Related U.S. Application Data

(63) Continuation of application No. 09/750,936, filed on Dec. 29, 2000, now abandoned.

(51) Int. Cl.
*A61K 6/00* (2006.01)
(52) U.S. Cl. .................................................. 424/401
(58) Field of Classification Search ................. 424/401
See application file for complete search history.

(56) References Cited

U.S. PATENT DOCUMENTS

| | | | | |
|---|---|---|---|---|
| 3,626,840 | A | * 12/1971 | Day | ............................ 99/355 |
| 5,688,839 | A | * 11/1997 | Royce | ........................ 523/171 |
| 5,721,306 | A | * 2/1998 | Tsipursky et al. | ........... 524/449 |
| 5,882,662 | A | * 3/1999 | Pahlck et al. | ................ 424/401 |
| 6,045,823 | A | * 4/2000 | Vollhardt et al. | ........... 424/450 |
| 6,183,760 | B1 | * 2/2001 | Travkina et al. | ............. 424/401 |
| 6,475,500 | B2 | * 11/2002 | Vatter et al. | ................. 424/401 |
| 6,524,598 | B2 | * 2/2003 | Sunkel et al. | ................ 424/401 |
| 6,660,277 | B1 | * 12/2003 | Fleissman | .................... 424/400 |
| 2002/0018760 | A1 | * 2/2002 | Vatter et al. | .............. 424/70.12 |
| 2006/0140895 | A1 | * 6/2006 | Zheng et al. | ............. 424/70.12 |

OTHER PUBLICATIONS

A Thomas, "Hydrogenation—Use in Frying Oils," SCI Lecture Papers Series, 1998, pp. 1-5.*
Answers.com, "Wax Material (in biology)", http://www.answers.com/wax&r=67, Dec. 18, 2006, 1 page.*

* cited by examiner

*Primary Examiner*—Sharon E. Kennedy
(74) *Attorney, Agent, or Firm*—Charles J. Zeller; Joan M. McGillycuddy; Anthony M. Santini

(57) ABSTRACT

There is provided a method of forming a segmented composition utilizing the thermal exchange properties of a first component that solidifies when cooled, and a second component that solidifies when heated. When an amount of the heat from the first component is transferred to the coolness of the second component, and vice versa, both the first and second components are provided with structural integrity, thus forming the segmented composition. There is also provided a method and an apparatus that can form a segmented cosmetic composition. The segmented cosmetic composition has at least two components. A first component is preferably a molten wax. A second component is preferably a smectite clay dispersion. One of the components fully surrounds, partially surrounds, or is adjacent to the other component.

48 Claims, 2 Drawing Sheets

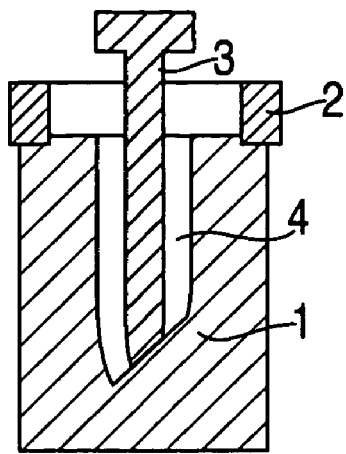
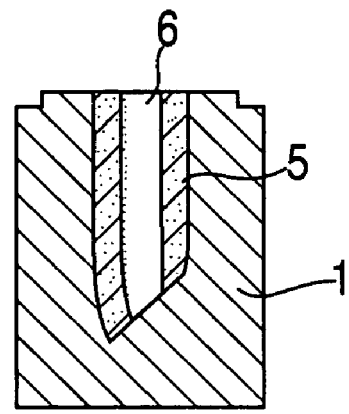
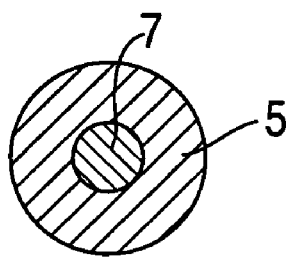
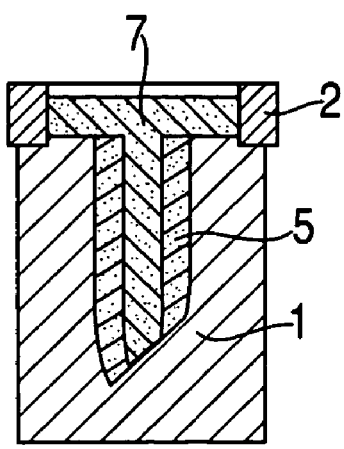
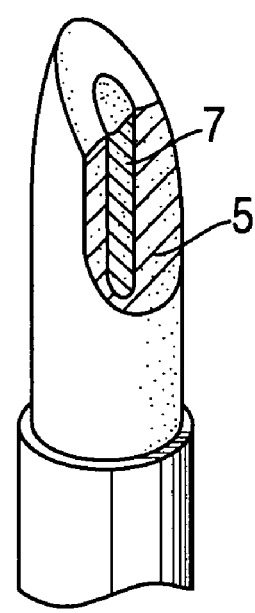
FIG. 1
FIG. 2
FIG. 4
FIG. 3
FIG. 5

SEGMENTED COMPOSITION AND A METHOD AND A SYSTEM FOR MAKING SAME

This is a continuation of application Ser. No. 09/750,936, filed Dec. 29, 2000 now abandoned.

BACKGROUND OF THE INVENTION

1. Field of the Invention

The present invention relates to compositions of the core-sheath type. More particularly, the present invention relates to cosmetic compositions having two or more components that are segmented therein. In addition, the present invention relates to the method of and apparatus for making such compositions.

2. Description of the Prior Art

Many consumers favor wax-free cosmetics. Wax-free cosmetics do not have a waxy feel or create a wax-like build-up. An example of a substantially wax-free cosmetic composition is provided in U.S. Pat. No. 5,882,662, issued on Mar. 16, 1999 to Pahlck et al., titled Cosmetic Compositions Containing Smectite Gels. This patent provides for a cosmetic composition comprising a smectite clay and a lipophilic polar solvent, which gels without the addition of a polar activator and without high shear.

However, many wax-free cosmetics lack the advantages inherent to wax-based cosmetics, which are preferred by many other consumers. Namely, wax-based cosmetics have high shine, soft feel, and good spreadability. Conventional wax-based lipsticks are manufactured by adding fats, oils, pigments or lakes, and other non-aqueous ingredients to a natural or synthetic hard wax base that is melted to enable the ingredients to be thoroughly mixed. Then, the mixed ingredients are cast into a mold that, after cooling, provides a cosmetic product, such as a lipstick.

Consumers would favor a cosmetic composition that could be molded to contain both the wax-based benefits of high shine, soft feel, and good spreadability, and the non-wax based benefits of no waxy feel and no wax-like build-up. However, the formation of such a cosmetic composition is problematic.

U.S. Pat. No. 4,291,018, which issued on Sep. 22, 1981 to Oeda et al., provides a lipstick of the core-sheath type having a first composition of low-viscosity, oily ingredients and a second composition of viscous, oily ingredients. This patent also discloses that, if the difference in melt (i.e. liquefying) temperatures between the two compositions is greater than 5° C., the desirable properties of each composition fails to be fully achieved.

Given the foregoing, a need exists for a segmented cosmetic composition that can combine the advantages and benefits of both wax-free and wax-based compositions. There is also a need for an efficient method of and apparatus for manufacturing such a cosmetic composition.

SUMMARY OF THE INVENTION

It is an object of the present invention to provide a composition that combines the advantages of both a wax-based component and a wax-free component.

It is another object of the present invention to provide a cosmetic composition that has at least two segments, each having either a wax-free component or a wax-based component.

It is still another object of the present invention to provide such a cosmetic composition that has at least two segments, one having a wax-free component and the other having a wax-based component.

It is yet another object of the present invention to provide such a composition in which the wax-free component is a smectite clay dispersion.

It is a further object of the present invention to provide a method and an apparatus that uses a thermal exchange between a hot liquid component and a cold liquid component to solidify the two components and form a segmented solid composition.

These and other objects of the present invention are achieved by a composition having at least two segments or components. The first component is preferably a cool, wax-free component. The second component is preferably a molten wax. One of the first or second components is adjacent to, partially surrounded by, or fully surrounded by the other component.

The present invention also includes a method of and an apparatus for forming such a segmented composition comprising a cool, liquefied or dispersed component that solidifies when heated in communication with a hot, liquefied or dispersed component that solidifies when cooled. The thermal exchange of heat from the hot liquid/dispersion component to the cold liquid/dispersion component and coolness of the cold liquid/dispersion component to the hot liquid/dispersion component, accelerates the solidification of the hot component and the cold component, thereby more rapidly forming the segmented composition. In other words, the heat from the hot component solidifies the cold component while the coolness from the cold component solidifies the hot component. As used herein, the terms "solidify", "solidifies" and variations thereof mean that the composition and/or component of the composition are provided with structural integrity by transferring/forming from a liquid/dispersion state to a solid or semi-solid state, or swelling to form a lattice-type structure.

BRIEF DESCRIPTION OF THE DRAWINGS

FIGS. 1 to 3 are sectional views illustrating a known molding apparatus for molding a lipstick of the core-sheath type;

FIG. 4 is a cross-sectional view illustrating the construction of the lipstick of FIG. 3;

FIG. 5 is a partial cutaway perspective view of the lipstick of FIG. 4;

DETAILED DESCRIPTION OF THE INVENTION

Figure 6:
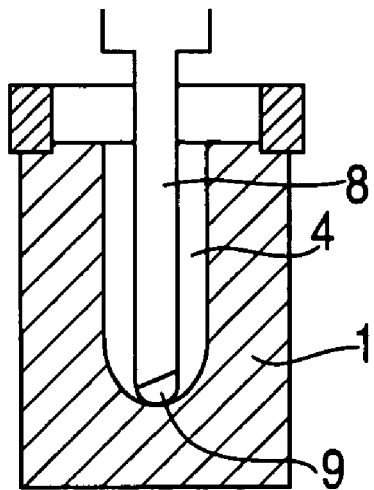
FIGS. 6 and 7 are sectional views of a preferred injection molding apparatus for use with the present invention.

The present invention provides a composition having at least two components. The components are preferably a hot component and a cool or cold component. The hot and cold components may be of any suitable ingredient or material that solidifies and provides structural integrity after they cool and warm, respectively. More preferably, the hot component is wax-based, while the cool component is wax-free. Moreover, the present invention provides for a method of and apparatus for using the thermal exchange properties of the two components during processing to form a segmented product. Such segmented products include many types of anhydrous and/or water-based cosmetic compositions, such as, for example, core-sheath type, pan type and marbleized type lipsticks and/or pomades; lip glosses; eyeshadows; concealers; moisturizers; skin care products; deodorants; and foundations.

The hot component of the present invention has a melting point preferably greater than about 50° C. (about 120° F.), more preferably greater than about 60° C. (about 140° F.). The hot component may use many different natural or synthetic waxes to provide structure to the final solid composition. The hot component of the present invention preferably includes one or more hard waxes having $C_8$ to $C_{50}$ hydrocarbons. A hard wax is one having a needle penetration in the range from about 2 millimeters to about 8 millimeters based on ASTM-D-1321. Hard waxes that can be used in the present invention include: carnauba, ozokerite, candelilla, paraffin, ceresin, lanolin, beeswax, polyethylene, and microcrystalline wax. Other examples of ingredients that contribute to the hard wax structure include: waxy esters such as behenyl behenate or behenyl erucate, fatty alcohols such as cetyl alcohol, fatty acids such as stearic acid, and jojoba oil. The wax of the present invention is most preferably a mixture of linear polyethylene and ozokerite.

The hot component may also include one or more ingredients that are not sensitive to heat. Such heat insensitive ingredients include: antioxidants; emollients and skin conditioning agents, such as fatty esters (for example, myristyl lactate, decyl oleate, and $C_{12}$ to $C_{15}$ alkyl benzoate), naturally derived oils (for example, avocado oil, chamomile oil, mink oil, squalane, and wheat germ glycerides), diisostearyl fumerate, lanolin, polytriglyceryl erucate/eleostearate, ginko biloba extract, zinc oxide, water, cholesterol, biotin, allantoin, milk protein, lauryl PCA, phospholipids, and mixtures thereof; silicones such as dimethicone and cyclomethicone; germicides; humectants such as glycerin; insect repellents; lipid materials; occlusives such as castor oil, canola oil, methicone including fatty dimethicone, petrolatum, polydecene, jojoba oil, jojoba wax, and jojoba butter; pigments; preservatives; emulsifiers; skin protectants; stabilizers; thickeners; UV-absorbers; and mixtures thereof.

The preferred emollients include avocado oil, diisostearyl fumerate, lanolin, myristyl lactate, polytriglyceryl erucate/eleostearate, and mixtures thereof.

The preferred preservatives or stabilizers include: BHT; BHA; 4-hydroxybenzoic acid, its esters and its derivatives, such as methyl 4 hydroxybenzoate (methyl paraben); benzophenones and its derivatives, such as 2,4-dihydroxybenzophenone; benzotriazole and its derivatives, such as 2-(2'-hydroxy-5'methylphenyl)-2H-benzotriazole; chlorphenesin; and disubstituted methane derivatives such as dianisoyl methane.

The preferred skin conditioners or conditioning agents include cholesterol, biotin, chamomile oil, ginko biloba extract, zinc oxide, allantoin, and mixtures thereof.

The cool or cold component of the present invention has a liquid dispersion point preferably less than about 15° C. (about 60° F.), more preferably less than about 13° C. (about 55° F.), and most preferably less than about 11° C. (about 52° F.). The cool component is preferably wax-free. When the cool component is wax-free, it preferably includes a smectite clay. More preferably, the smectite clay is a synthetic smectite clay powder. The preferred synthetic smectite clay powder is lithium/magnesium/sodium silicate.

An example of such a lithium/magnesium/sodium silicate smectite clay is Lucentite SAN, which is manufactured by Co-op Chemical Co., Ltd. and distributed in the U.S. by Kobo Products, Inc., South Plainfield, N.J. Lucentite SAN is a powder having about 60 percentage by weight (wt %) to about 70 wt % lithium/magnesium/sodium silicate with the general structure:

$$Na_{0-0.33} (Mg_{2.67} Li_{0.33}) (Si_4O_4) (OH)_2$$

and about 30 wt % to about 40 wt % quaternium-18, which has the general structure:

$$R_2N(CH_3)_2$$

where R is $C_{16}$ to about $C_{18}$.

In the preferred embodiment of the present invention, the smectite clay powder is dissolved in a liquid, such as water, an organic solvent, or an oil, to form a dispersion. The chosen liquid depends on the type of smectite clay used.

The smectite clay powder is preferably dissolved in an organic solvent, which is preferably a polar lipophilic hydrocarbon-based solvent. Organic solvents useful as solvents in the present invention include: acetates, alcohols, aliphatic hydrocarbons, phenyl di- and tri-methicones, benzoate esters and other aromatic hydrocarbons, salicylate esters, alcohol lactates (such as $C_{12-15}$ alcohol lactate), ethers, formamides, halogenated hydrocarbons, ketones, methacrylates, phthalates, sulfoxides, and mixtures thereof. An example of a preferred benzoate ester useful in the present invention is a $C_{12}$ to $C_{15}$ alcohols benzoate. Such a $C_{12}$ to $C_{15}$ alcohols benzoate is available as Finsolv Tenn., manufactured by Finetex, Inc., Elmwood Park, N.J., and disclosed in U.S. Pat. Nos. 4,275,222; 4,278,655; 4,293,544; 4,322,545; and 4,323,694. U.S. Pat. No. 5,882,662 to Pahlck et al., which is incorporated herein by reference, provides details on the gelling of smectite clays with a $C_{12}$ to $C_{15}$ alkyl benzoate.

An example of a preferred ether useful as an organic solvent in the present invention is perfluoropolymethylisopropyl ether. Such an ether is available as Fomblin HC/R, manufactured by Ausimont SPA and distributed in the U.S. by Brooks Distribution Division, Inc., South Plainfield, N.J.

In a preferred embodiment of the present invention, about 10 wt % to about 50 wt % of the smectite clay powder is mixed with about 50 wt % to about 90 wt % of the organic solvent. More preferably, about 15 wt % to about 20 wt % of the smectite clay powder is mixed with about 80 wt % to about 85 wt % of the organic solvent. In a most preferred embodiment, about 18 wt % of the smectite clay powder is mixed with about 82 wt % of the organic solvent.

Optionally, heat sensitive ingredients can be added to the cool, wax-free component. These ingredients include: alcohols, ascorbyl phosphoryl, cholesterol, bioflavonoids, botanicals, fragrances, vitamins including vitamins A, B1, B2, B12, C and D3, perfloro-compounds, permethyl-compounds, pheromones, collagens, preservatives, retinols (such as retinyl palmitate), silicones, volatile compounds, yeast, and any derivatives thereof and any mixtures thereof. These ingredients can be active when added in an amount effective for providing a benefit associated with the ingredient.

Preferred vitamins include beta-carotene, tocopherol, vitamins A, B1, B2, B12, C and D3, and mixtures thereof. In the case of heat sensitive active ingredients, they can be incorporated into a solid, segmented composition without thermally degrading the active. This is a significant advance with respect to such compositions.

A method of forming a segmented cosmetic composition in accordance with the most preferred embodiment of the present invention is as follows:

The hot component is prepared by melting, for example, a conventional wax base and optionally mixing the melted wax base with one or more additional ingredients. Preferably, the hot component is maintained at about 70° C. to about 90° C. (about 160° F. to about 195° F.), more preferably at about 80° C. to about 85° C. (about 175° F. to about 185° F.), in liquefied form until it is added to a molding apparatus. The cold component of the present invention is created, for example, by dissolving the smectite clay powder in the organic solvent to form a dispersion. The smectite clay dispersion may be pumpable, injectable or pourable depending on the amount of smectite clay used and the temperature at which the smectite clay is processed. Since the smectite clay dispersion is liquid when cold and solidifies at room temperature or above, it is preferably chilled during formulation to maintain it in liquefied form. This may be achieved by cooling the whole dispersion or by cooling the solvent before the powder is added to form the dispersion. Preferably, the cold component is maintained at about −4° C. to about 13° C. (about 25° F. to about 55° F.), more preferably at about 0° C. to about 5° C. (about 32° F. to about 40° F.), until it is added to the molding apparatus. Optionally, the cold component can be mixed with one or more heat-sensitive ingredients. The difference in the temperature point at which the hot component and cold component become liquefied/dispersed is at least 10° C. to about 85° C., preferably about 25° C. to about 70° C., more preferably about 30° C. to about 50° C., and most preferably about 35° C. to about 45° C.

The present method uses a molding apparatus divided into two or more segments by an insert or separator. For example, the mold may have a first segment that surrounds a second segment in a core-sheath relationship. Alternatively, the first segment may be adjacent to, or only partially surrounding, the second segment.

In one embodiment of the method of the present invention, as illustrated in FIGS. 1 to 5, a known mold comprises a lower part 1 having a cavity 4 for molding the body of a lipstick, and an upper part 2 for introducing the compositions thereto. As shown in FIG. 1, a rod 3 is inserted into the cavity 4 to form a core. The molten wax-based component 5 is then poured into the cavity 4 and allowed to partially "set-up". As is known by those skilled in the art, the term "set-up" means that the composition begins to solidify as its temperature approaches room temperature. Thereafter, the rod 3 is removed. Consequently, a core cavity 6 is molded as illustrated in FIG. 2. The cold, wax-free component 7, as shown in FIG. 3, is then poured unto the core cavity 6. The molten wax-based component 5 is juxtaposed to the cold, wax-free component 7. Heat from the molten, wax-based component 5 and coolness from the cold, wax-free component 7 are conducted/exchanged, which simultaneously causes the wax-based component 5 to cool and the wax-free component 7 to warm. Upon cooling to approximately room temperature, the molten wax-based component 5 completely sets-up and solidifies. Similarly, upon warming to approximately room temperature, the cold wax-free component 7 swells and binds against the wax sheath and solidifies. The solidification forms a segmented lipstick product having a wax-based component 5 as the outer sheath and a wax-free component 7 as the core, as shown in FIGS. 4 and 5. Alternatively, the cold, wax-free component 7 can form the outer sheath and the hot, wax-based component 5 can form the core.

The thermal exchange or exchange system of the present invention rapidly accelerates the manufacture of a segmented composition and obviates the need for other equipment, such as a chill table, typically used with hot melt products. Cosmetic products of the core-sheath type having a variety of shapes can be produced by changing the cross-sectional shapes of the cavity 4 and the rod 3 in the above-described mold. The cross-sectional shapes of the core and the sheath may be, for example, circular, elliptic, oval, triangular, square, rectangular, pentagonal, hexagonal, rhombic, or any intricate shape as a result of the flowable properties of the components. However, a substantially concentric construction is preferred because of the ease of formation.

The foregoing method could be varied to form other types of cosmetic products. For example, both the hot, wax-based component and the cold, wax-free component could be simultaneously poured into the mold cavity (without the use of any rod or separator). The heat conducted from the hot or molten component to the cold component, and vice versa, would simultaneously set up the cold, component and the molten component. The hot, wax-based component and cool, wax-free component could then be blended shortly before the components are fully set, thereby creating a marbleized product.

Figure 7:
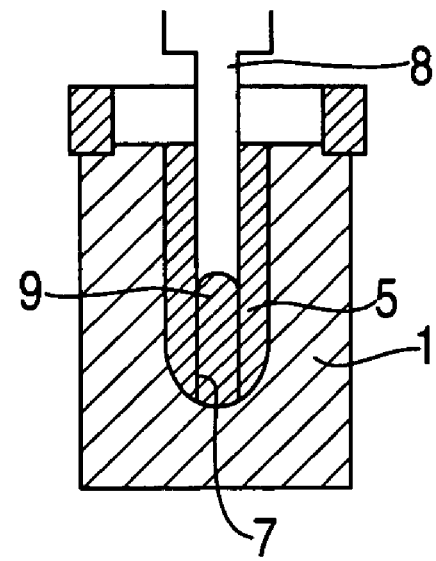

In an alternative embodiment of the present invention, the segmented composition can be made by an injection molding apparatus shown in FIGS. 6 and 7. In one form of the injection molding apparatus, a hollow injector 8 having a dispensing nozzle 9 is inserted into cavity 4 of mold 1. The molten component 5 is poured by any conventional means, such as by a human's hand, a container, a manual device or an automatic device, into cavity 4 and allowed to partially set-up as a sheath about injector 8. Injector 8 is then withdrawn by any conventional means, such as, a human's hand, a manual device, and an automatic device, from cavity 4. As shown in FIG. 7, as injector 8 is withdrawn, the cold component 7 is dispensed though hollow injector 8 and discharged through dispensing nozzle 9 into a core cavity formed by the volume of injector 8. Once the injector 8 is fully withdrawn, the cold component fully fills the core cavity, as depicted in FIG. 3. The thermal exchange of the present invention rapidly accelerates the formation of a segmented composition, as described herein.

In a second form of the injection molding apparatus, the injector 8 is withdrawn from cavity 4 immediately after the molten component 5 is poured therein, without any set-up time. As injector 8 is withdrawn, the cold component 7 is discharged to fill the volume occupied by injector 8 to maximize the amount of heat available for exchange to the cold component and the amount of coolness available for exchange to the molten component, thereby providing even greater acceleration of the solidification of the segmented compositions. The second form of the injection molding apparatus works best when the two components are of sufficiently different densities and/or specific gravities to allow one component to remain as a centrally located core and not become substantially miscible with the other outer sheath component. The injection molding apparatus can also be used to back-fill or top-fill pan-type or jar-type structures.

In another embodiment of the apparatus and system of the present invention, a non-removed, or permanent, hollow insert made of the core component material can be used to integrally form the core of the segmented composition. Alternatively, the hollow insert can be made of the sheath material and used to integrally form the sheath of the segmented composition. For example, if it was decided to make the sheath from the hot component material (that solidifies as it cools), and the core from the cold component material (that solidifies as it warms), the rod 3 of FIG. 1 can be replaced with a hollow insert made of the cold component material, which maintains its solid form when warmed. The molten sheath component material is then poured into cavity 4. Since the sheath component material is hot, it will have no adverse effect on the hollow insert, which is relatively thin but has sufficient structural integrity to support the forces of the hot sheath component material acting on its outer periphery. Into the hollow insert is then poured the cold core component material. As the cold core component is made of the same material as the hollow insert, the coolness of the cold core component material can immediately begin to liquefy/disperse the hollow insert on its inner periphery. However, the simultaneous effect of the heat from the molten sheath component material will maximize the thermal exchange between the two components resulting in an immediate set-up of the components at their interface and a rapid acceleration of the solidification of the entire segmented composition.

Figure 8:
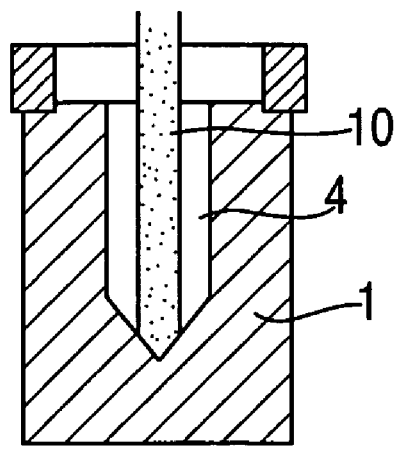
FIG. 8 is a sectional view of an alternative preferred embodiment of a molding apparatus using a perforated hollow core insert.

In another aspect of this embodiment, the non-removed hollow core insert described above can be made of a core or sheath component material that remains in its solidified state even upon re-exposure to heat or cold, as the case may be. For example, the solid hollow insert can be made of a cold, liquid dispersion that solidifies upon exposure to warmth, but does not re-liquefy/disperse upon re-exposure to cold. In this embodiment, the non-reversible insert can be perforated, as shown in FIG. 8. By making the hollow insert 10 perforated, the heat from the hot sheath component material can more quickly pass to the cold core component material, and vice-versa, and rapidly accelerate the solidification of the segmented composition, while remaining an integral part of the core component. It is to be understood that the above-described non-removed, solid hollow insert may be made of any dissolvable or non-dissolvable material that will serve the same temporary membrane-type function, provided the material will be compatible with the intended use of the final product. In a further aspect of this embodiment, a dissolvable membrane may be of a material that sublimates upon contact with the second component poured into the cavity.

It has been unexpectedly found that a segmented composition can be formed using the thermal exchange between a first component that is a liquid when heated and solidifies when cooled to room temperature or below and a second component that is a liquid when cold and solidifies when warmed to room temperature or above. The utilization of the thermal exchange between the two components is useful for the manufacture of numerous consumer products, such as core-sheath cosmetic products, especially lipsticks, set forth above.

Having thus described the present invention with particular reference to the preferred forms thereof, it will be obvious that various changes and modifications may be made without departing from the spirit and scope of the present invention as defined in the appended claims.

Wherefore it is claimed:

1. A method of making a segmented composition comprising the steps of:
contacting a first wax-based composition, the first wax-based composition being heated to a temperature at which the first wax-based composition is molten, with a second composition containing smectite clay dispersed in a solvent, the second composition being cooled to a temperature below the temperature at which it will set up, the difference between the temperature of the first composition and the temperature of the second composition, at the time of contacting, defining a temperature differential that provides a heat exchange between the contacted compositions which causes the first composition to cool and the second composition to warm thereby accelerating solidification of the first composition and set up of the second composition so that upon cooling to about zoom temperature the first composition solidifies and the second composition swells, binds to the first composition and sets up to form the segmented composition.

2. The method of claim 1, wherein said first wax-based composition becomes molten at a temperature about 50° C. or greater.

3. The method of claim 2, wherein said second composition is a liquid dispersion at a temperature about 15° C. or less.

4. The method of claim 1, wherein said wax-based composition contains a natural or synthetic wax.

5. The method of claim 1, wherein said wax-based composition contains one or more hard waxes having $C_8$ to $C_{50}$ hydrocarbons.

6. The method of claim 1, wherein said wax-based composition contains a wax selected from the group consisting of: carnauba, ozokerite, candelilla, paraffin, ceresin, lanolin, beeswax, polyethylene, microcrystalline wax, and any combination thereof.

7. The method of claim 1, wherein said second composition is wax-free.

8. The method of claim 7, wherein said solvent is an organic solvent.

9. The method of claim 8, wherein said organic solvent is selected from the group consisting of one or more: acetates, alcohols, aliphatic hydrocarbons, aromatic hydrocarbons, ethers, formamides, halogenated hydrocarbons, phenyl di- and tri- methicones, ketones, methacrylates, phthalates, sulfoxides, and any mixtures thereof.

10. The method of claim 8, wherein said smectite clay is present in an amount about 10 wt% to about 50 wt% and said organic solvent is present in an amount about 50 wt% to about 90 wt%, based on the total weight of the second composition.

11. The method of claim 3, wherein said first wax-based composition and said second composition have a liquefying/dispersing temperature differential of at least 10° C. to about 85° C.

12. The method of claim 11, wherein the temperature differential is about 30° C. to about 50° C.

13. The method of claim 1, further comprising adding to said second composition a heat sensitive active ingredient in an active effective amount.

14. The method of claim 13, wherein the active ingredient is selected from the group consisting of bioflavonoids, botanicals, fragrances, silicones, yeast, pheromones, collagen, ascorbyl phosphoryl, cholesterol, vitamins A, B1, B2, B12, C and D3, any derivatives thereof and any mixtures thereof.

15. The method of claim 1, wherein the segmented composition is selected from the group consisting of a lipstick, pomade, lip gloss, eyeshadow, concealer, moisturizer, skin care product, deodorant, and foundation.

16. The method of claim 1, further comprising the steps of liquefying said first wax-based composition and said second composition and placing the first and second compositions in contact with one another in a mold so that a heat exchange takes place between the first wax-based composition and the second composition, said heat exchange accelerating solidification of the first composition and set up of the second composition.

17. The method of claim 16, wherein the liquefying temperature of said first wax-based composition is greater than about 60° C., and wherein the liquefying temperature of said second composition is less than about 15° C.

18. The method of claim 16, wherein said first and said second compositions have a liquefying temperature differential of at least about 10° C. to about 85° C.

19. The method of claim 18, wherein the temperature differential is about 30° C. to about 50° C.

20. The method of claim 16, wherein the liquefied first wax-based composition is placed into said mold at a temperature from about 70° C. to about 90° C.

21. The method of claim 20, wherein the liquefied/dispersed second composition is placed into said mold at a temperature from about −4° C. to about 13° C.

22. The method of claim 16, wherein said first and said second compositions form discrete first and second segments of the segmented when the first and second compositions are at room temperature.

23. The method of claim 16, further comprising blending said first and said second compositions before the first composition is completely solidified and the second composition is fully set up, to create a marbleized segmented composition.

24. The method of claim 16, wherein said second composition is wax-free.

25. The method of claim 22, wherein the mold is configured so that the first and second segments are juxtaposed in a core-sheath arrangement.

26. The method of claim 22, further comprising the steps of
(a) inserting a hollow injector having a dispensing nozzle into a cavity of said mold;
(b) placing one of said first and said second compositions into said cavity to form a sheath at least partially about said injector;
(c) withdrawing said injector from said cavity to form a cavity core; and
(d) dispensing the other of said first and said second compositions from said dispensing nozzle into said cavity core as said injector is withdrawn.

27. The method of claim 22, further comprising the steps of
(a) inserting a rod into a cavity of said mold;
(b) placing one of said first and said second compositions into said cavity to form a sheath at least partially about said rod;
(c) withdrawing said rod from said cavity to form a cavity core; and
(d) placing the other of said first and said second compositions into said cavity core.

28. The method of claim 22, further comprising the steps of
(a) placing a solid hollow insert made of said first or said second composition into a cavity of said mold;
(b) placing the other of said first and said second compositions into said cavity to form a sheath at least partially about said hollow insert; and
(c) placing the other of said first and said second compositions into said hollow insert.

29. The method of claim 22, further comprising the steps of
(a) placing a perforated, hollow insert made of said first or said second composition into a cavity of said mold;
(b) placing one of said first and said second compositions different from said hollow insert into said cavity to form a sheath at least partially about said hollow insert; and
(c) placing the other of said first and said second compositions into said hollow insert.

30. The method of claim 22, further comprising the steps of
(a) placing a solid hollow insert into a cavity of said mold;
(b) placing one of said first and second compositions, different from said hollow insert, into said cavity to form a sheath at least partially about said hollow insert;
(c) placing the other of said first and said second compositions into said hollow insert; and
(d) at least partially sublimating said hollow insert upon contact with said other of said first and said second compositions.

31. The method of claim 8, wherein the smectite clay dispersion sets up when the temperature of the second composition is above its liquefying/dispersing temperature.

32. The composition made by the process of claim 1.

33. The composition made by the process of claim 31.

34. A segmented composition comprising a first wax-based composition having a liquefying temperature of about 50° C. or greater, the first wax-based composition solidifying at a temperature below its liquefying temperature, and a second composition which at a liquefying/dispersing temperature of less than about 15° C. is a liquid dispersion, the second composition setting up above its liquefying/dispersing temperature, wherein said first and said second compositions are in contact with each other, and one of said first and said second compositions is adjacent to, partially surrounded by or fully surrounded by the other of said first and said second compositions, contact between the first and second compositions being such that heat exchange between the first and second compositions accelerates solidification of the first composition and set up of the second composition so that when the first and second compositions are at room temperature, said first and said second compositions form two discrete segments of the segmented composition, wherein the segmented composition is a cosmetic selected from the group consisting of core-sheath type, pan type, and marbleized type lipsticks, lip glosses, eyeshadows, concealers, moisturizers, deodorants, and foundations.

35. The composition of claim 34, wherein said second composition is wax-free.

36. The composition of claim 34, wherein the liquefying/dispersing temperature of said first composition is greater than about 60° C., and wherein the liquefying/dispersing temperature of said second composition is less than about 13° C.

37. The composition of claim 34, wherein said first and said second compositions have a liquefying temperature differential of at least about 10° C. to about 85° C.

38. The composition of claim 37, wherein the temperature differential is about 30° C. to about 50° C.

39. The composition of claim 34, wherein the first composition is liquefied and is placed into a mold at a temperature from about 70° C. to about 90° C.

40. The composition of claim 39, wherein the second composition is a liquid dispersion and is placed into said mold at a temperature from about −4° C. to about 13° C.

41. The composition of claim 34, wherein said first end said second compositions form discrete juxtaposed first and second segments of the segmented composition upon being fully set-up.

42. The composition of claim 34, wherein the segmented composition is marbleized.

43. The composition of claim 42, wherein said second composition is wax-free.

44. The composition of claim 43, wherein said second composition is a smectite clay dispersed in a solvent.

45. The composition of claim 44, wherein the smectite clay dispersion sets up at or above its liquefying/dispersing temperature.

46. A segmented composition comprising:
  a molten first wax-based composition having a first temperature that is above the temperature at which the wax-based composition liquefies; and
  a liquefied dispersed second composition comprising a smectite clay, the second composition being at a second temperature that is lower than said first temperature and lower than its liquefying/dispersing temperature, the second composition setting up at a temperature above its liquefying/dispersing temperature, the first wax-based composition and the second composition being juxtaposed so that a heat transfer will occur between the first wax-based composition and the second composition accelerating solidification of the first wax-based composition and set up of the second composition so that, at room temperature, the first composition and the second composition form two discrete segments of the segmented composition.

47. The composition of claim 46, wherein said first temperature is about 70° C. to about 80° C. and said second temperature is about −4° C. to about 13° C.

48. The composition of claim 46, wherein the smectite clay is dispersed in a solvent, the dispersion being capable of setting up when the temperature is above the second temperature.

* * * * *